(12) United States Patent
Bierhoff et al.

(10) Patent No.: US 8,324,562 B2
(45) Date of Patent: Dec. 4, 2012

(54) FIBER SCANNING SYSTEM HAVING A MAGNET ATTACHED TO THE FIBER AT A POSITION BEFORE OR AFTER AN ELECTRICAL COIL WITH IMPROVED TIP POSITIONING

(75) Inventors: Waltherus Cornelis Jozef Bierhoff, Eindhoven (NL); Bernardus Hendrikus Wilhelmus Hendriks, Eindhoven (NL); Augustinus Laurentius Braun, Eindhoven (NL); Nanad Mihajlovic, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 428 days.

(21) Appl. No.: 12/668,905

(22) PCT Filed: Jul. 14, 2008

(86) PCT No.: PCT/IB2008/052821
§ 371 (c)(1), (2), (4) Date: Jan. 13, 2010

(87) PCT Pub. No.: WO2009/013663
PCT Pub. Date: Jan. 29, 2009

(65) Prior Publication Data
US 2010/0207015 A1 Aug. 19, 2010

(30) Foreign Application Priority Data
Jul. 20, 2007 (EP) .................................. 07112833
Nov. 27, 2007 (EP) .................................. 07121670

(51) Int. Cl.
*H01J 3/14* (2006.01)

(52) U.S. Cl. .................................. 250/234; 250/227.26
(58) Field of Classification Search .................. 250/234, 250/235, 227.11, 227.2–227.26; 385/25, 385/902; 600/473–478
See application file for complete search history.

(56) References Cited

U.S. PATENT DOCUMENTS
3,530,258 A * 9/1970 Johnson et al. ............ 369/44.19
(Continued)

FOREIGN PATENT DOCUMENTS
CN 1376443 A 10/2002
(Continued)

OTHER PUBLICATIONS
E.J. Siebel et al, "A Full-Color Scanning Fiber Endoscope", Optical Fibers and Sensors for Medical Diagnosis and Treatment Applications, Ed. I Gannot, Proc. SPIE, vol. 6083.

*Primary Examiner* — Que T Le

(57) ABSTRACT

A fiber scanning system is provided comprising a housing (102) with a fiber (13), the fiber (13) comprising a fixed part and a free end, the fixed part being attached to a bottom of the housing (102) and the fiber (13) extending parallel to the wall of the housing (102). At least one electrical coil (12) is attached to the wall at a position in between the fixed part and the free end of the fiber (13), a winding of the electrical coil (12) being in a plane parallel to the fiber (13). A magnet (11) is attached to the fiber (13), such that the electrical coil (12) may induce a force on the magnet (11). The magnet (11) is attached to the fiber (13) at a position just before or after the electrical coil (12), a width of the magnet (11) being such that the magnet (11) extends over the electrical coil (12).

13 Claims, 12 Drawing Sheets

U.S. PATENT DOCUMENTS

| | | |
|---|---|---|
| 5,317,148 A | 5/1994 | Gray et al. |
| 6,294,775 B1 | 9/2001 | Seibel et al. |
| 6,564,087 B1 | 5/2003 | Pitris et al. |
| 6,608,684 B1 | 8/2003 | Gelikonov et al. |
| 6,967,772 B2 | 11/2005 | Harris |
| 7,010,978 B1 | 3/2006 | Harris et al. |
| 7,123,790 B2 | 10/2006 | Rosman et al. |
| 2003/0206321 A1 | 11/2003 | Gelikonov et al. |
| 2005/0027163 A1 | 2/2005 | Chin et al. |
| 2006/0285791 A1 | 12/2006 | Piyevsky et al. |
| 2007/0019906 A1 | 1/2007 | Melville |

FOREIGN PATENT DOCUMENTS

| | | |
|---|---|---|
| EP | 0782027 | 7/1997 |
| WO | WO2004040267 | 5/2004 |
| WO | WO2006013528 | 2/2006 |

* cited by examiner

FIBER SCANNING SYSTEM HAVING A MAGNET ATTACHED TO THE FIBER AT A POSITION BEFORE OR AFTER AN ELECTRICAL COIL WITH IMPROVED TIP POSITIONING

FIELD OF THE INVENTION

The present invention relates to a fiber scanning system comprising a housing with a fiber, the fiber comprising a fixed part and a free end, the fixed part being attached to a bottom of the housing and the fiber extending parallel to the wall of the housing. At least one electrical coil is attached to the wall at a position in between the fixed part and the free end of the fiber, a winding of the electrical coil being in a plane parallel to the fiber. A magnet is attached to the fiber, such that the electrical coil may induce a force on the magnet. In particular the invention relates to an optical fiber scanning system for obtaining images or spectral measurements of tissue.

BACKGROUND OF THE INVENTION

For correct diagnosis of various cancer diseases biopsies are taken. This can either be via a lumen of an endoscope or via needle biopsies. An example of a needle biopsy is shown in FIG. 7, where a biopsy is taken from the prostate via the rectum. In order to find the correct position to take the biopsy, various imaging modalities are used such as X-ray, MRI and ultrasound. In case of prostate cancer in most cases the biopsy is guided by ultrasound (see FIG. 7). Although helpful, these methods of guidance are far from optimal. The resolution is limited and, furthermore, these imaging modalities can in most cases not discriminate between benign and malignant tissue. As a result we do not know for certain whether from the correct part of the tissue a biopsy is taken. We take almost blind biopsies and even if after inspection of the tissue no cancer cells are detected, we do not know for certain that we did not simply miss the right spot to take the biopsy.

In order to improve the biopsy procedure direct inspection of the biopt position prior of taken the biopt is required. A way to achieve this is by microscopic inspection at this position. This requires a miniaturized confocal microscope. In the publication in Optical Fibers and Sensors for Medical Diagnosis and Treatment Applications, Ed. I Gannot, Proc. SPIE vol. 6083 the article "A full-color scanning fiber endoscope", by E. J. Seibel et al., a fiber scanning fiber endoscope (see FIG. 8) a fiber scanning system based on a piezo actuator is described. A drawback of this system is that it is operated in a resonant way. Apart from being fast, a resonant scanner has two drawbacks. The first is that scanning pattern is fixed (see FIG. 9). If a certain part of the image is of interest only or if you want to measure at a fixed position you always have to scan the complete object. Especially in the case of spectral imaging and two-photon spectral imaging some time is required to collect the photons to have sufficient statistics. Also the needed relatively high voltage of ~75 Volt poses additional constraints for, e.g., an endoscope or catheter.

Another drawback is that, due to resonance mode, the position of the end tip of the fiber depends strongly on the properties of the fiber. Small differences in the manufacturing of the fiber will affect the scanning properties. Another drawback is that the deflection of the fiber tip is limited in case of resonant scanning The longer the fiber the slower the scanning and the larger the fiber part beyond the actuating device. A longer fiber makes the system tolerance sensitive and the risk of other modes than the resonant mode is high. This means that resonant scanning is less preferred.

In U.S. Pat. Nos. 6,967,772 and 7,010,978, a scanning fiber system is described based on an electrically operated tuning fork. Again this system is operated in resonance mode with some of the drawbacks as mentioned above. Furthermore, the tuning fork makes the system rather bulky limiting the downscaling of the system.

In U.S. Pat. No. 7,123,790, a scanning fiber system is described using four electrical coils with windings in a plane perpendicular to the fiber. The system of U.S. Pat. No. 7,123,790 uses a resonant driving method for scanning the fiber tip in an elliptical pattern.

It is a disadvantage of the above described fiber scanning systems, that they employ resonance scanning of the fiber resulting in a system in which the area to be scanned cannot be easily adjusted and in which the position of the fiber tip is less well-defined.

In U.S. Pat. No. 5,317,148, a permanent magnet, attached to an optical fiber, is enclosed by two electromagnet pairs with windings in a plane parallel to the fiber. By controlling the voltage to each of the magnets, the exact position of the permanent magnet is controlled. As a result, the position of the free end of the optical fiber is controlled to scan a target area using various patterns. It is a disadvantage of the system disclosed in U.S. Pat. No. 5,317,148 that it is relatively large and that is not suitable for miniaturization. For example, for medical applications miniaturization is an important aspect in order to minimize tissue damage during examination of the patient.

SUMMARY OF THE INVENTION

It is an object of the present invention to provide a fiber scanning system that mitigates one or more drawbacks of the prior art systems. More particular, it is an object of the invention to provide a very small non-resonant fiber scanning system. Therefore, in the system according to the invention, the magnet is attached to the fiber at a position just before or after the electrical coil, a width of the magnet being such that the magnet extends over the electrical coil. As a result of the small distance between the magnet and the electrical coil, the resulting force is relatively large. Consequently, the fiber tip can be put in any position within the scanning area. It can operate in scanning mode or can remain fixed in a well-defined position. Because the deflection of the fiber is defined by the actuator (magnet—electrical coil combination) and not by the resonance properties of the fiber, the position of the tip is well defined.

A further aspect of the invention is that the fiber can also scan in a resonant mode. This allows image formation at a fast time scale and if required a spectrum can be measured of a certain point of the tissue at a longer time scale. This dual mode scanning is of particular importance for tissue inspection where image formation and spectral measurements are required i.e. for optical biopsy.

A further aspect of the invention, as shown in FIG. 10, is that the magnet is preferably attached to the fiber and the coils are attached to the housing.

The fiber may be arranged to guide light. In this way the system can be used to obtain an image or to obtain spectral measurement from tissue in front of the system.

A further aspect of the invention is that the fiber scanning system is used in a medical system, such as an endoscope, a catheter, a biopsy or other type of needle.

These and other aspects of the invention are apparent from and will be elucidated with reference to the embodiments described hereinafter.

DETAILED DESCRIPTION OF THE INVENTION

Figure 1:
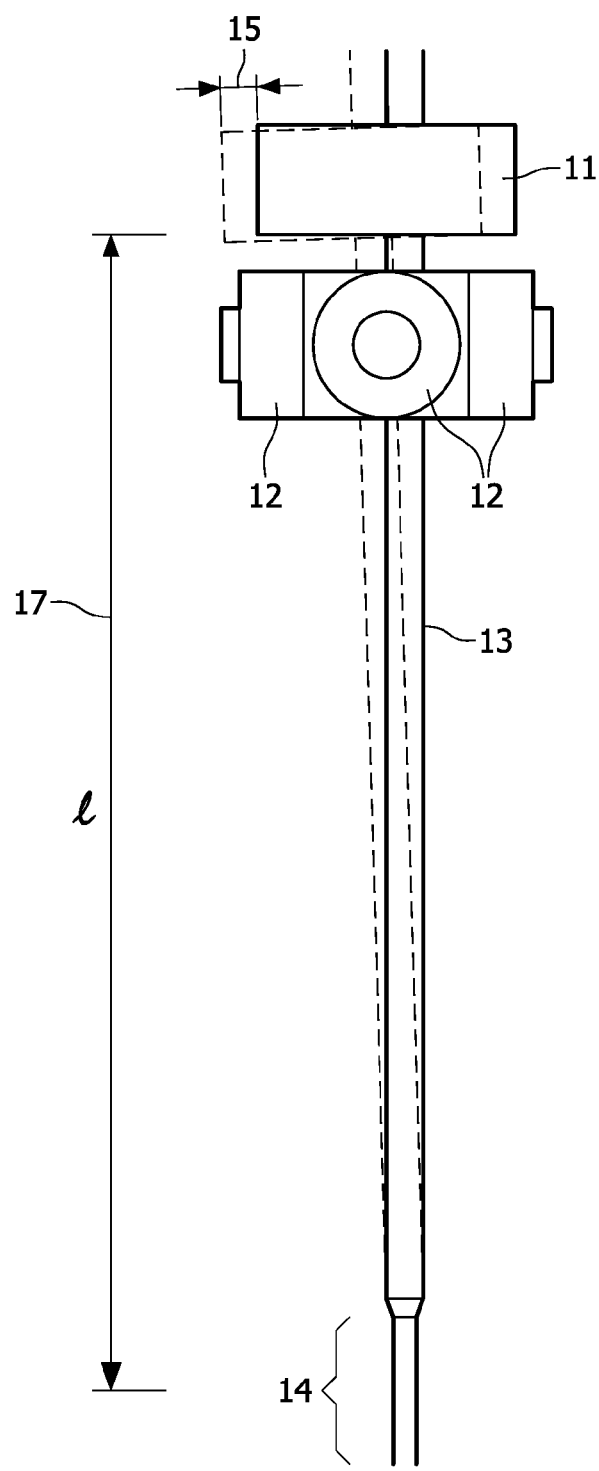
FIG. 1 shows the actuator part of a fiber scanning system according to the invention.

In a first embodiment the scanner consists of fiber with two magnets mounted on it. In the housing 102 of the scanner four coils 12 are mounted that do not contact the fiber 13. The fiber 13 itself is mounted in a centering ring 101 that is connected to the housing 102 (see FIG. 10). When a current is applied to one of the coils 12, due to Lorenz forces, the magnet 11 will be pushed in one or the other direction depending on the direction of the current. By applying the current sequentially in the coils 12 the fiber tip can be placed in any wanted position within the working area. This is shown in FIG. 11.

Furthermore, it is possible to use only one magnet instead of two and to use 3 coils instead of 4 coils. With two oppositely placed coils or even with one coil and one magnet, line scanning in one direction is possible.

The stroke of the end of the fiber tip depends on the length between the cantilever point and the position of the motor (actuator) and the free length of the fiber above the motor part. See L1 and L2 in FIG. 12. The stroke of the end of the fiber tip further depends on the dimensions of the housing, and the electromagnetic coupling between magnets and coils.

The length L2 also determines the resonance frequency and the achievable stroke in the resonance mode. By changing the cantilever position with respect to the motor and the length of the free end of the fiber the stroke and frequency can be changed (see FIG. 13).

FIG. 1 shows the actuator of the scanning system according to the invention. The actuator comprises the magnet 11 and the electrical coils 12. The magnet may be a permanent magnet or a piece of ferromagnetic material that becomes magnetized in the proximity of a magnetic field. The fiber 13 bends in the indicated bending area 14, due to forces between the magnet 11 attached to the fiber 13 and the coils 12 attached to the housing. This results in a travel 15 of the magnet 11 and the fiber 13 with respect to the housing.

Figure 2:
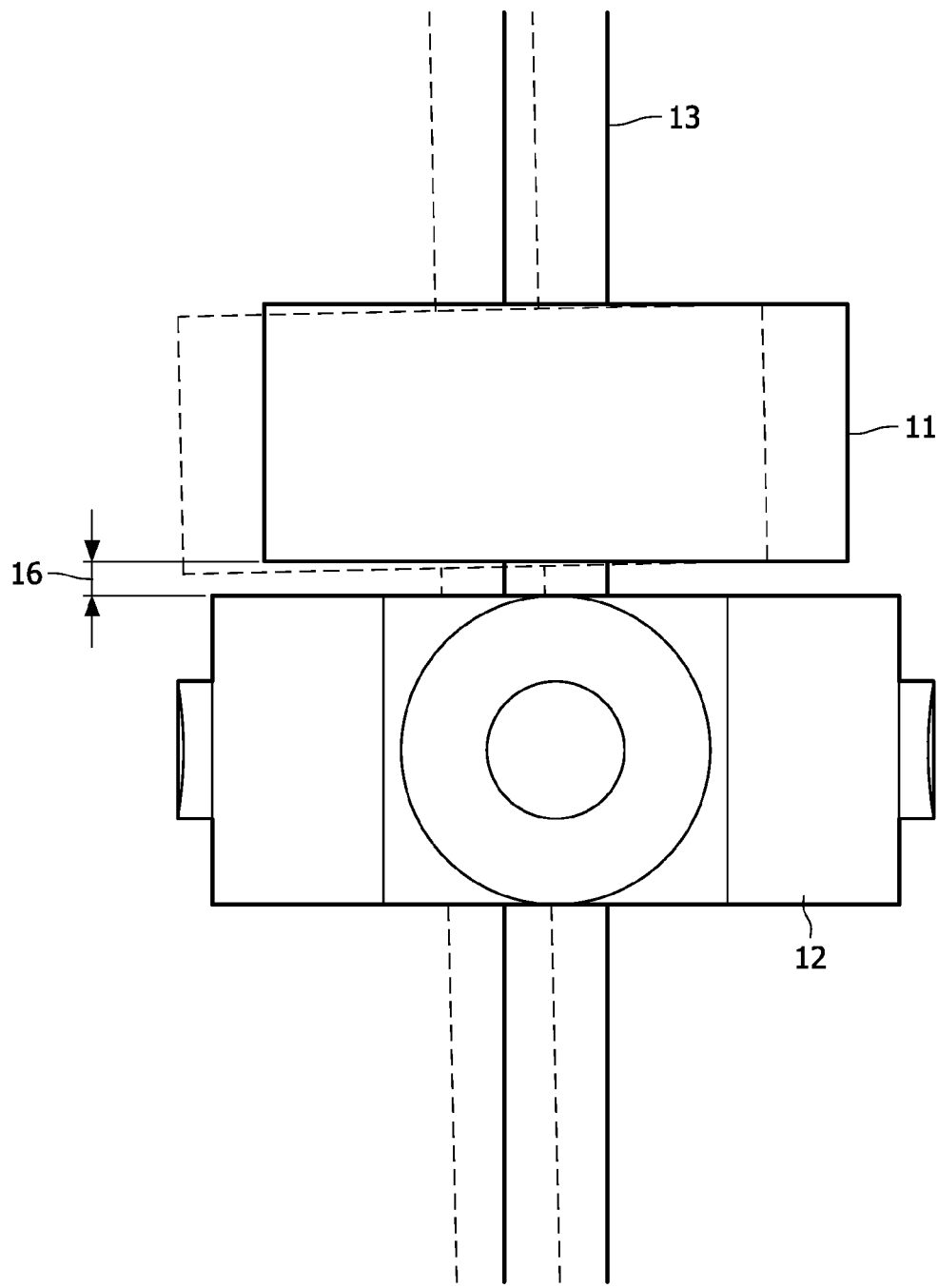
FIG. 2 shows the actuator in greater detail.

FIG. 2 shows in greater detail the coils 12 and the magnet 11 of the actuator. The windings of a coil 12 lie in a plane parallel to the fiber 13 and the orientation of the coil 12 is orthogonal to the fiber 13. The magnetizing direction (NS direction) of the magnet 11 is parallel to the fiber 13. The resulting force between a coil 12 and the magnet 11 when a current flows through the coil 12 is orthogonal to the fiber 13, making the magnet 11 travel as indicated. The size of the magnet 11 is such that it is close to the coils 12 during its travel, resulting in a small air gap 16 between the coils 12 and the magnet 11. Because the air gap 16 is small, the resulting force is relatively large making it possible to fix the fiber 13 in a desired position. As can be seen in FIG. 1, the path traveled by the magnet 11 is circular. However, since the radius 17 is relatively large, the path is almost a straight line. This makes that the air gap 16 is almost constant during the travel and that it therefore can be chosen very small. So the force is then large and constant during the travel. For proper operation, the air gap 16 should at least be larger than 5 micrometer to avoid the movement of the magnet 11 being obstructed by the coils 12. Preferably, the air gap 16 is between 50 and 100 micrometer wide. Larger air gaps 16 result in smaller forces. In the embodiment of FIG. 2, the magnet 11 size is such that, in equilibrium position, the magnet extends over approximately 50% of the coil length. For stronger forces, the magnet should be large and extend over the coils as much as possible. However, due to mechanical constraints, a larger magnet may decrease the freedom of movement for the fiber tip. Preferably, the magnet extends at least over 10% of the coil length.

Figure 3:
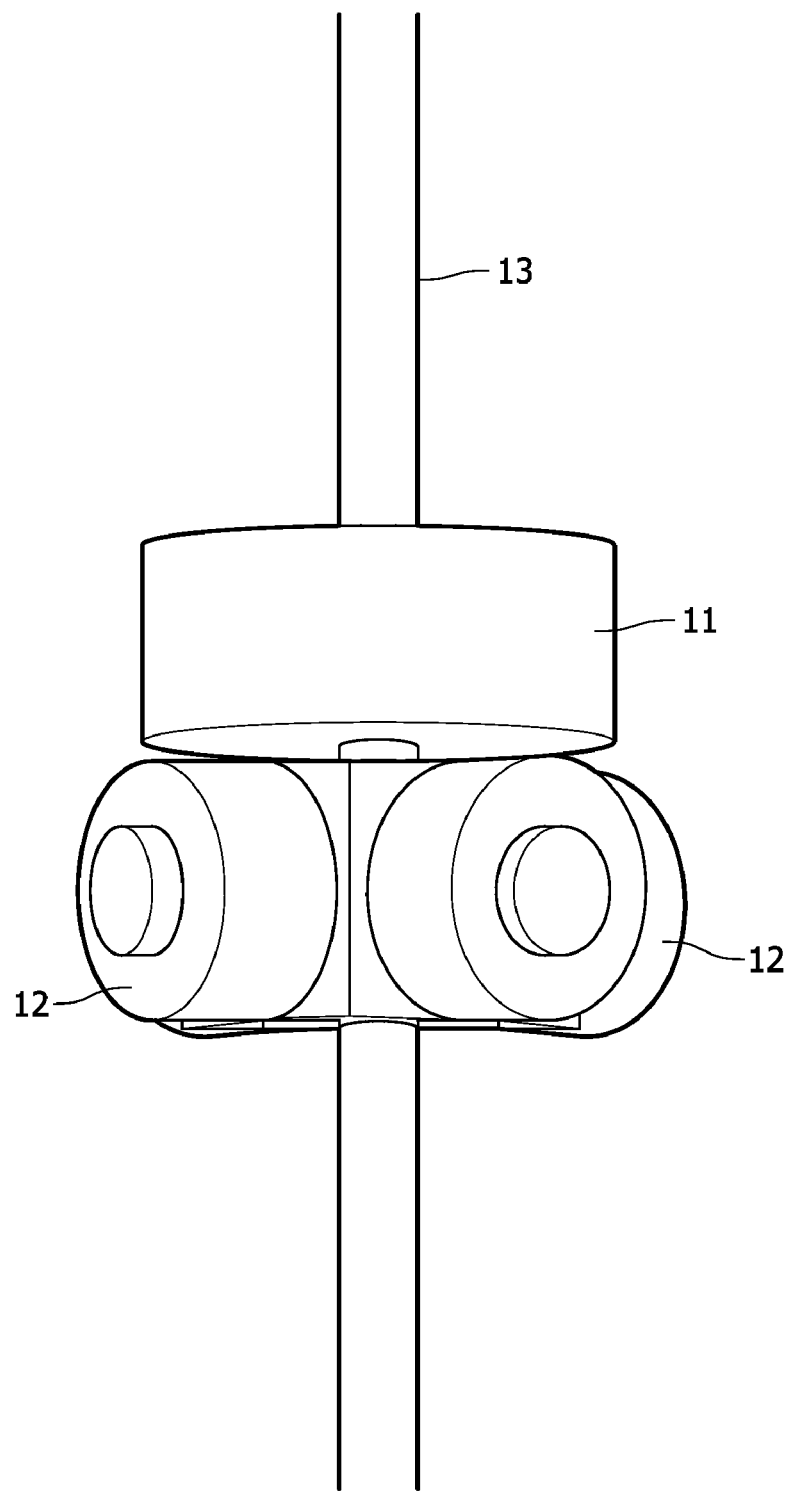
FIG. 3 shows the actuator part in perspective.

FIG. 3 shows in perspective an embodiment where the magnet 11 and fiber 13 can be scanned, i.e. positioned, in two directions with respect to the coils 12 that are fixed to the housing (not shown). To this end, four coils 12 and a disk-shaped magnet 11 are used in this embodiment.

Figure 4:
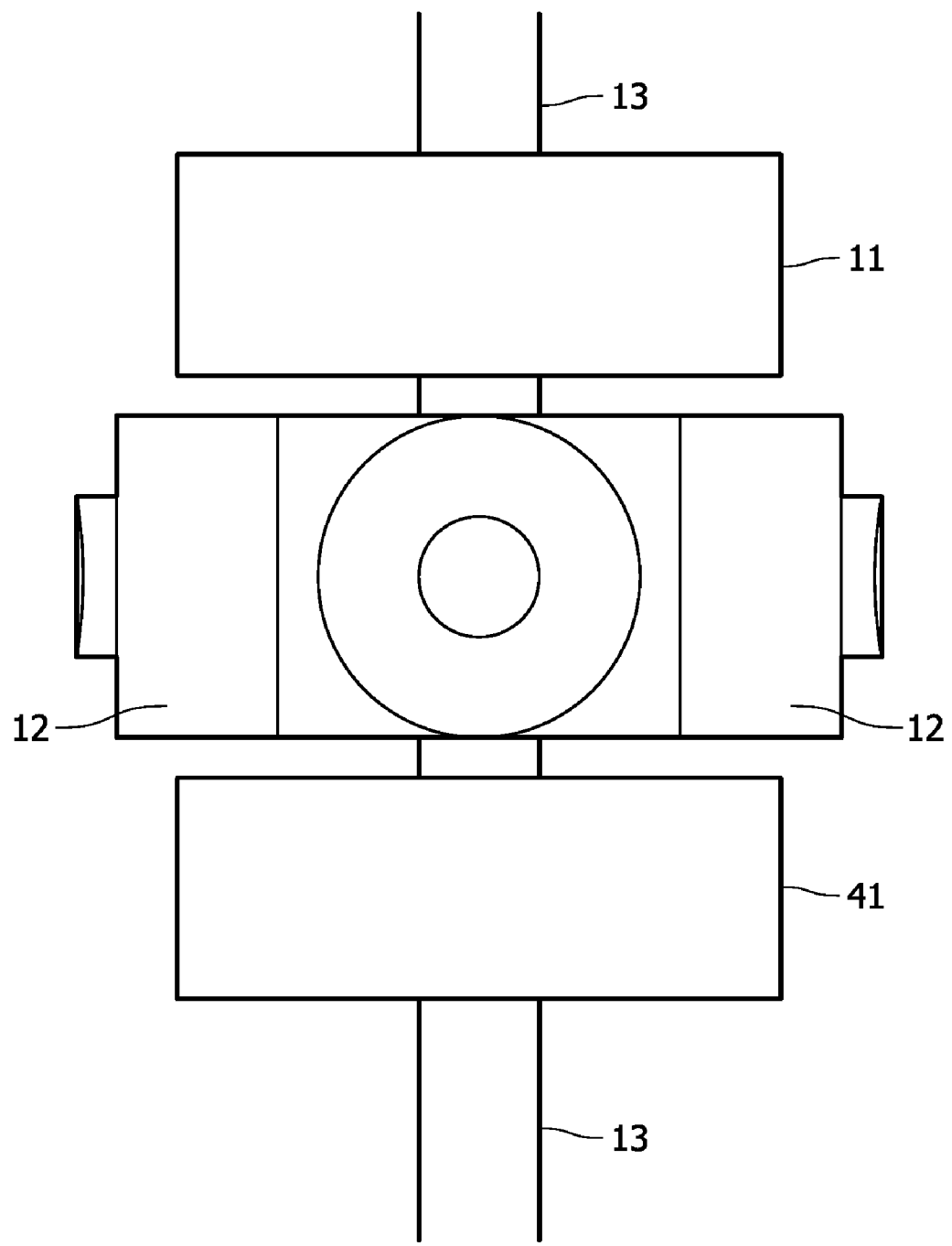
FIG. 4 shows an actuator with two magnets.

FIG. 4 shows and embodiment with two magnets 11, 41. Here the forces that drive the fiber 13 are nearly doubled with respect to FIG. 2.

Figure 5:
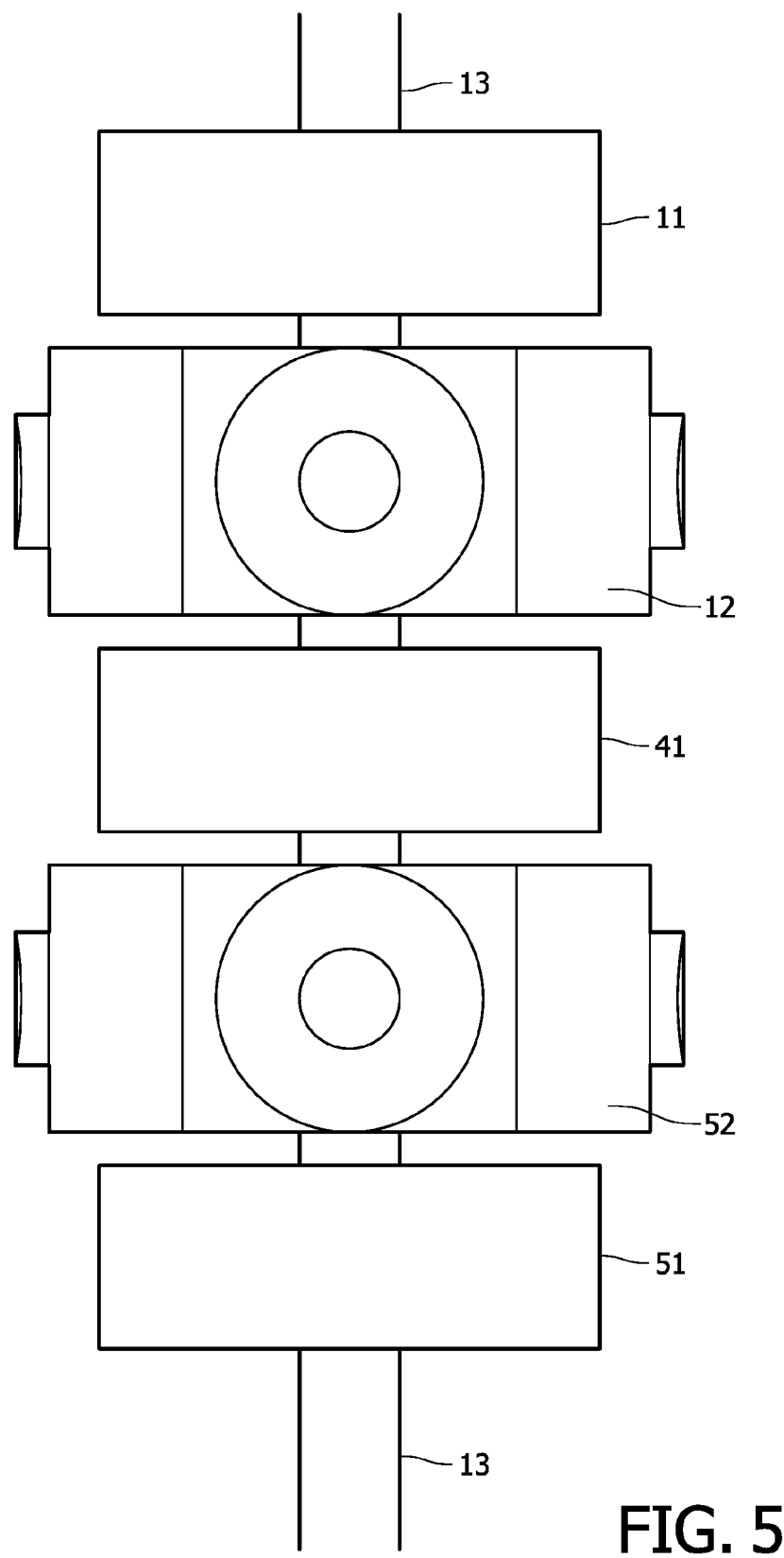
FIG. 5 shows an actuator with three magnets and two sets of electrical coils.

FIG. 5 shows an embodiment with two sets of coils 12, 52 and three magnets 11, 41, 51 to further increase the force on the fiber 13.

Figure 6:
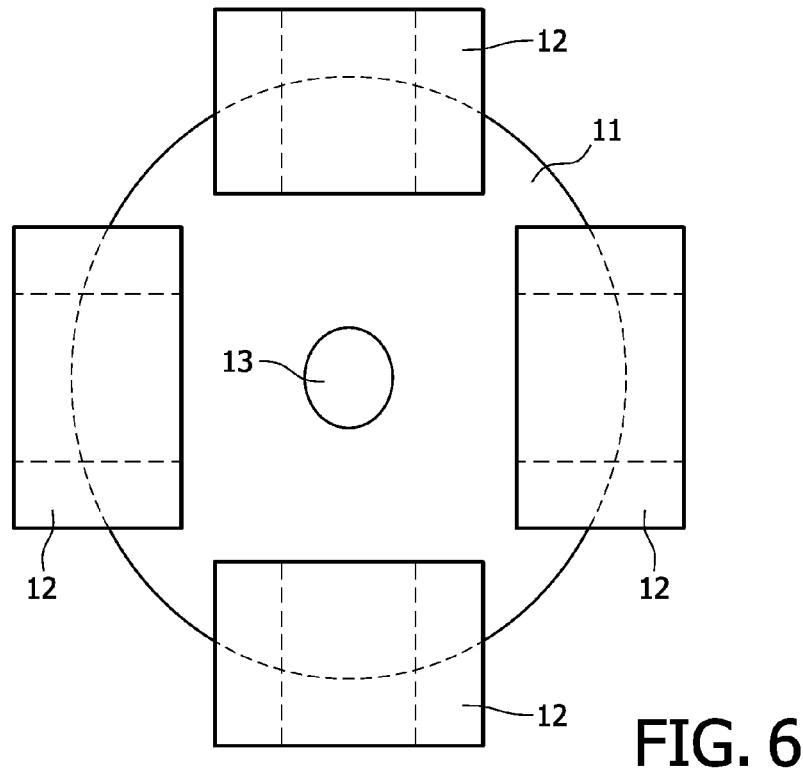
FIG. 6 shows a top view of the actuator according to the invention.
Figure 7:
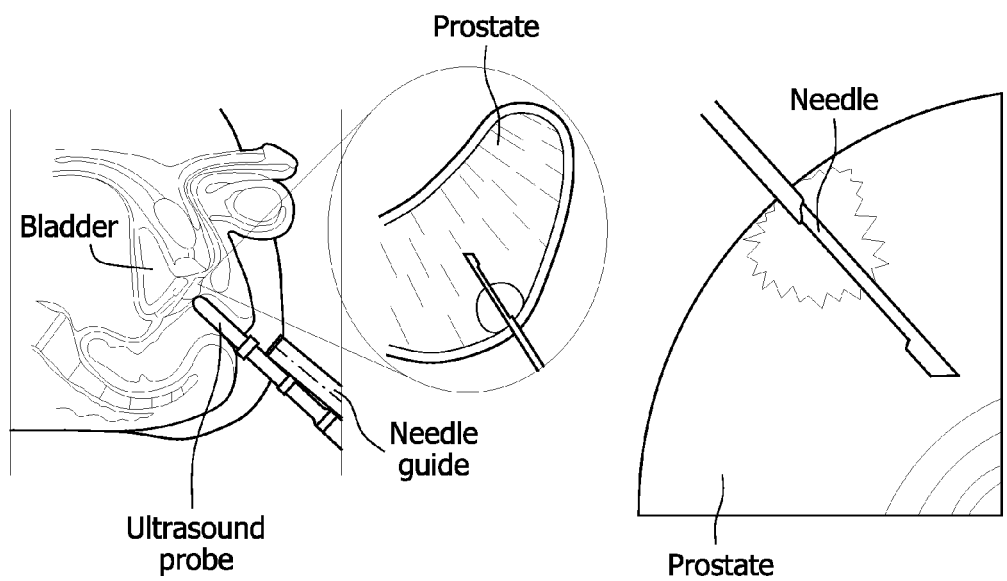
FIG. 7 shows a schematic drawing of taking a biopsy via the rectum under ultrasound guidance (prior art)
Figure 8:
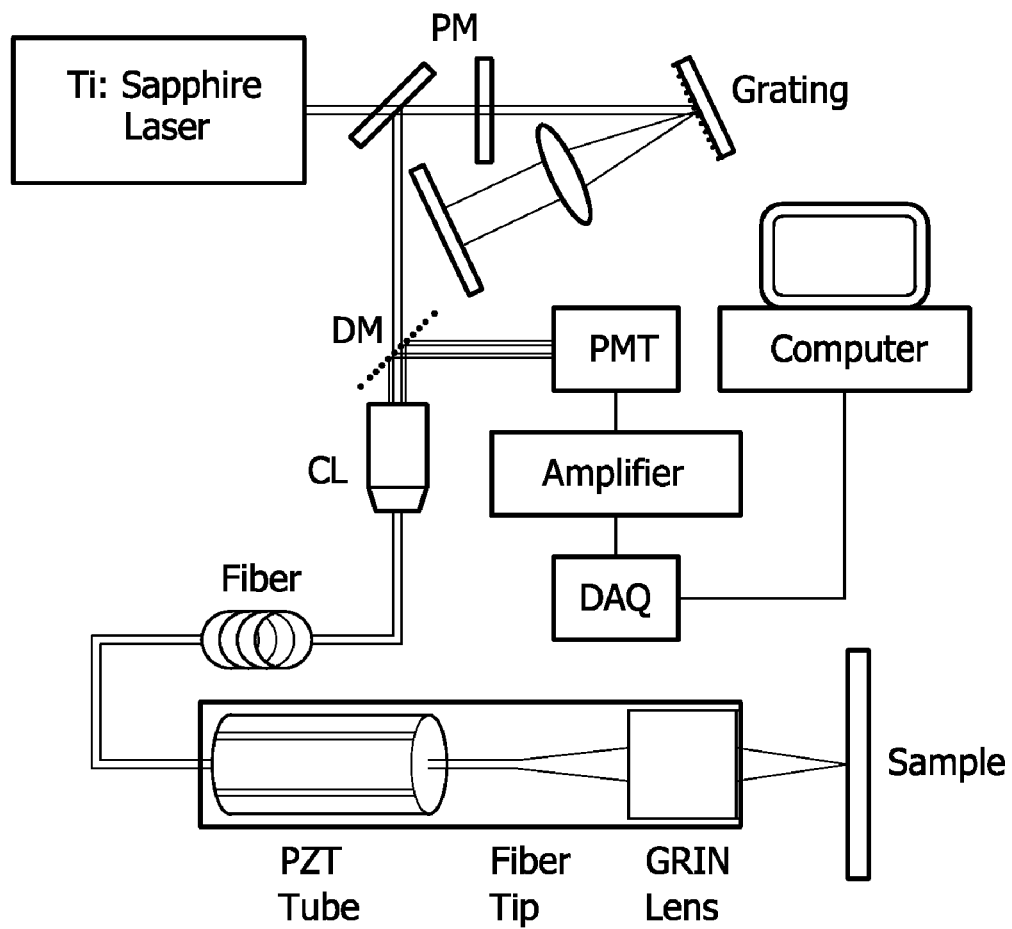
FIG. 8 shows a scanning system consisting of a laser coupled to a fiber, where the fiber is coupled to a scanning system (prior art)

FIG. 6 shows a top view of the actuator according to the invention. It clearly shows the relatively large area available for moving the fiber 13 between the four coils 12. This makes that a relatively large area can be scanned by the system according to the invention. Line scanning in one dimension is already possible when using only one of the four coils 12. Scanning in two directions requires at least two non parallel and preferably orthogonally placed coils 12.

Figure 10:
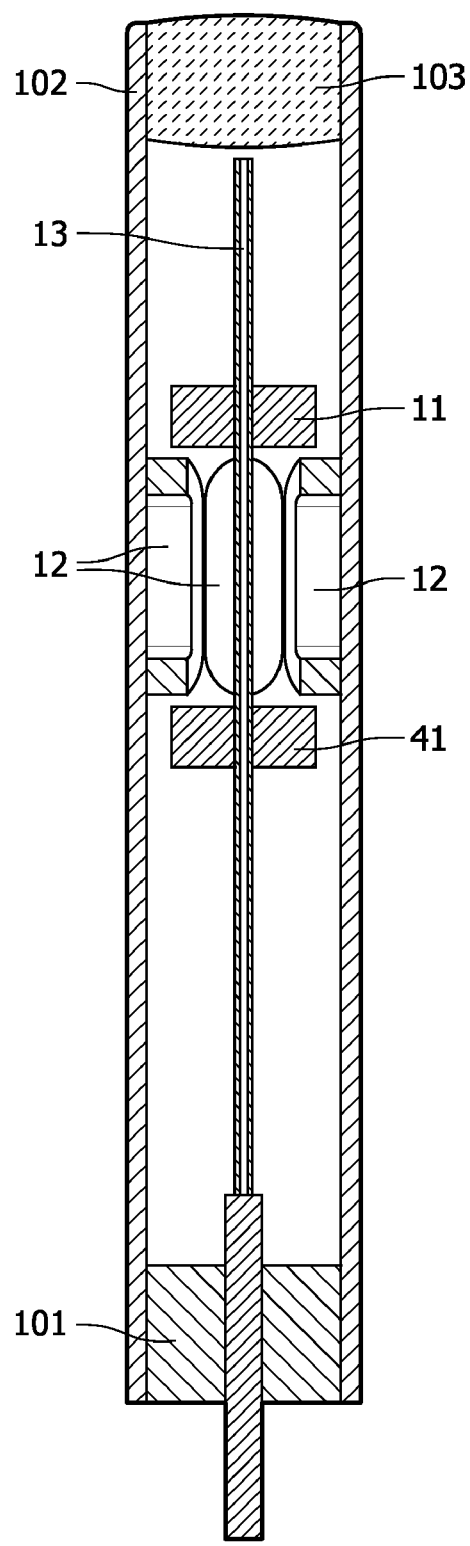
FIG. 10 shows an embodiment of the fiber scanning system according to the invention.
Figure 11:
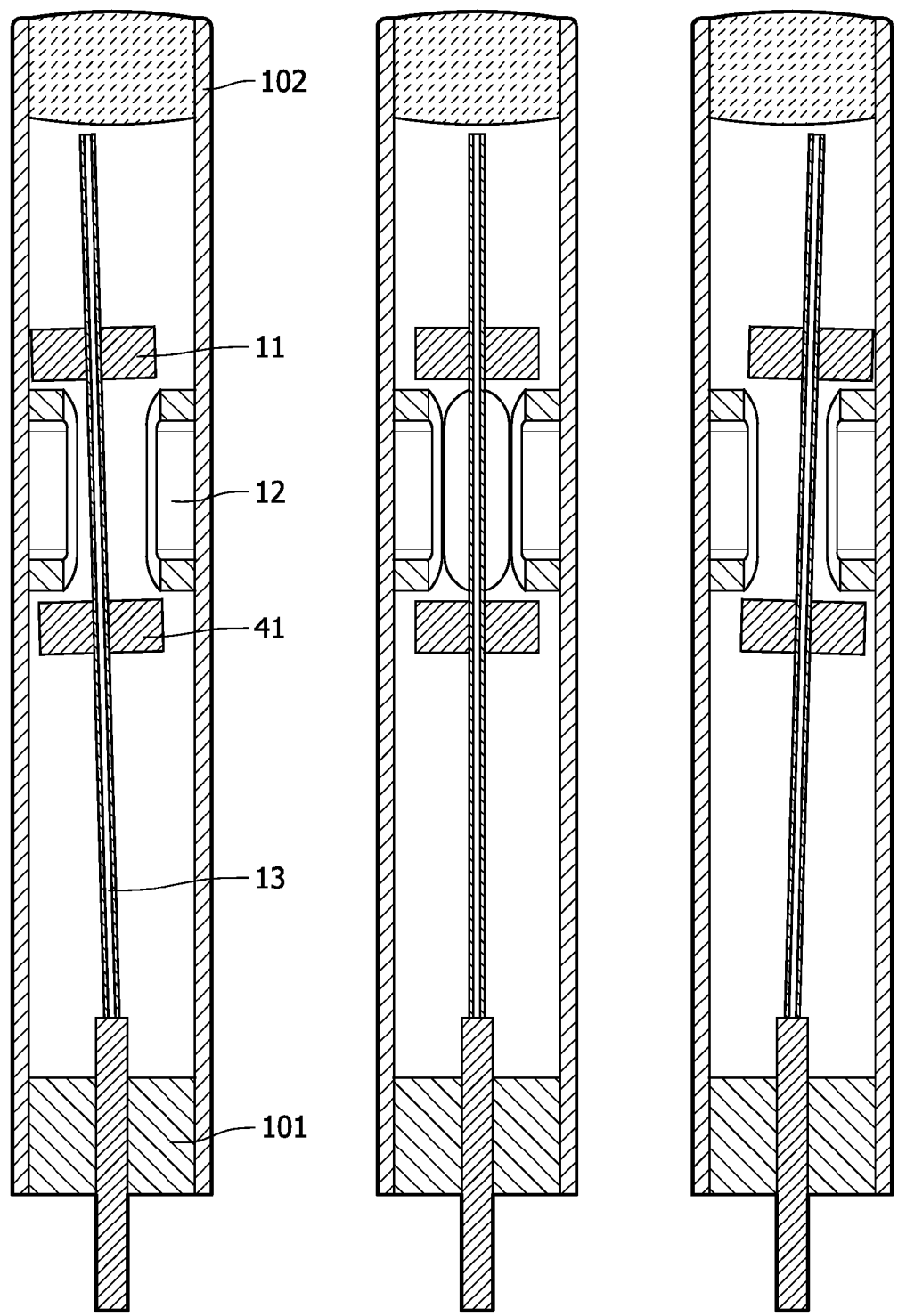
FIG. 11 shows an embodiment of the fiber scanning system according to the invention with the fiber tip in three different positions.

FIG. 10 shows an embodiment of a fiber scanning system according to the invention. One end of the fiber 13 is attached to the housing 102. The free end of the fiber 13 is situated close to a lens 103 for focusing light at a target area. Two magnets 11, 41 are attached to the fiber 13. In between the magnets 11, 41, a set of coils 12 is attached to the housing 102. The coils 12 and the magnets 11, 41 are arranged such that the coils 12 can induce a force on the magnets 11, 41 to push or pull the fiber tip to a desired position.

FIG. 11 shows the embodiment of FIG. 10 with the fiber tip in three different positions. In the most left figure, the current through the coils 12 is such that the resulting magnetic field pushes or pulls the magnets 11, 41 to the left.

Figure 12:
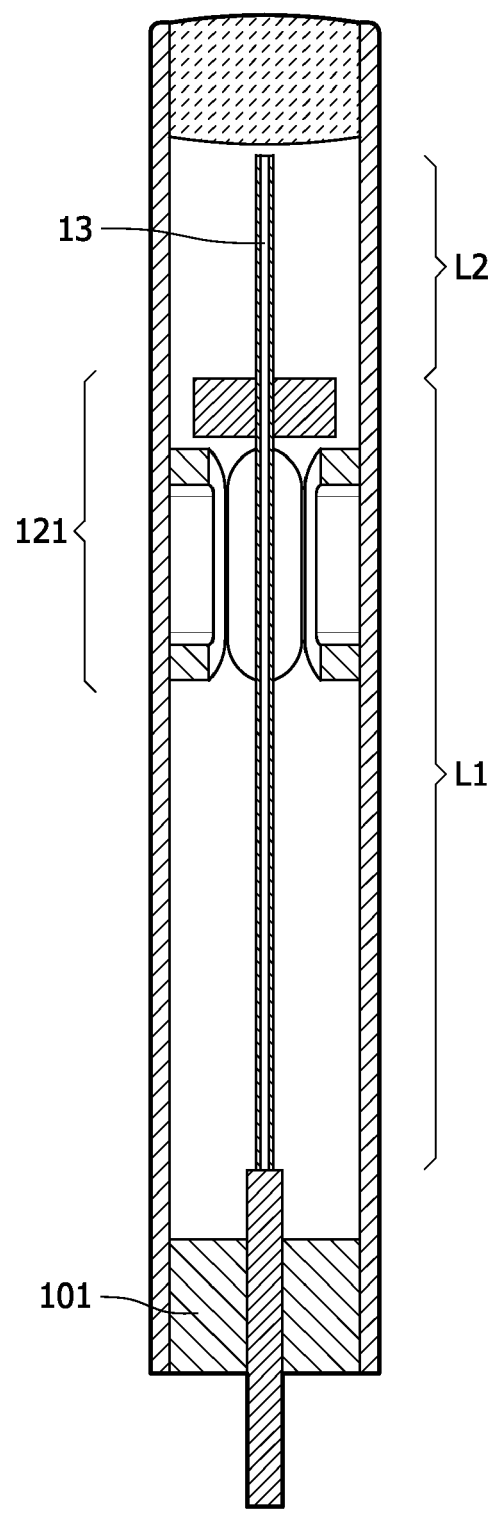
FIG. 12 shows an embodiment of the fiber scanning system according to the invention with adjustable distances between the centering ring, magnet and fiber tip.

FIG. 12 shows an embodiment of the fiber scanning system according to the invention with adjustable distances between the centering ring, magnet and fiber tip. The fiber 13 is attached to the housing at the centering ring 101 and bends in the fiber part close to the centering ring 101. The stroke, of the end of the fiber tip, is depending on the length between the centering ring 101 and the position of the actuator 121 and the free length of the fiber 13 above the actuator part 121. See L1 and L2 in FIG. 12. The length L2 also determines the resonance frequency and the achievable stroke in the resonance mode. By changing the position of the centering ring 101 with respect to the actuator part 121 and the length of the free end of the fiber, the stroke and frequency can be changed.

Figure 13:
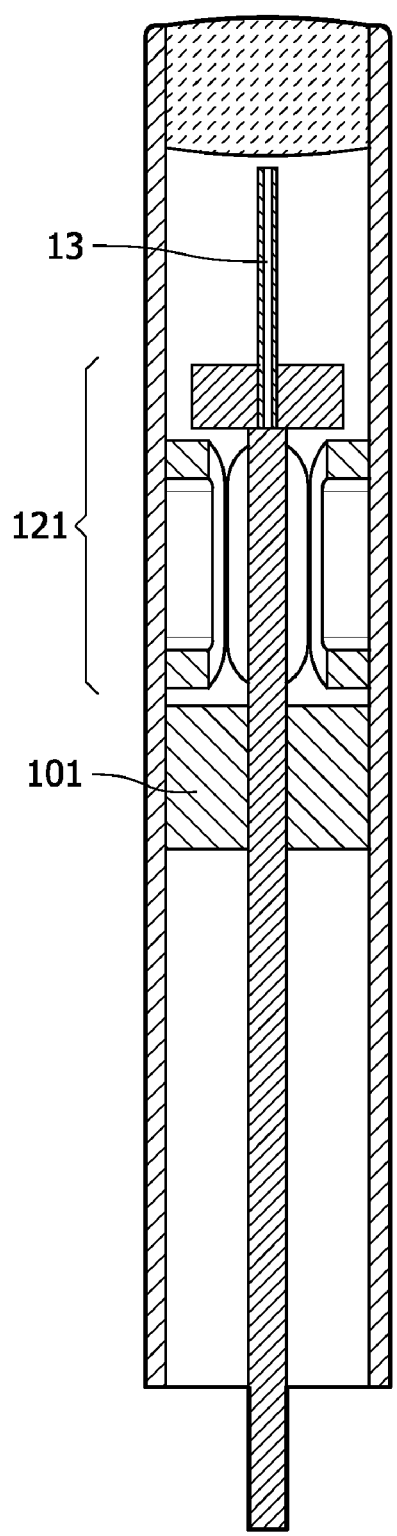
FIG. 13 shows the embodiment of FIG. 12 with adjusted distances.

FIG. 13 shows the embodiment of FIG. 12 with adjusted distances. The centering ring 101 is moved towards the actuator part 121, thereby making the length L1 very small and increasing the stroke of the fiber tip.

Figure 9A:
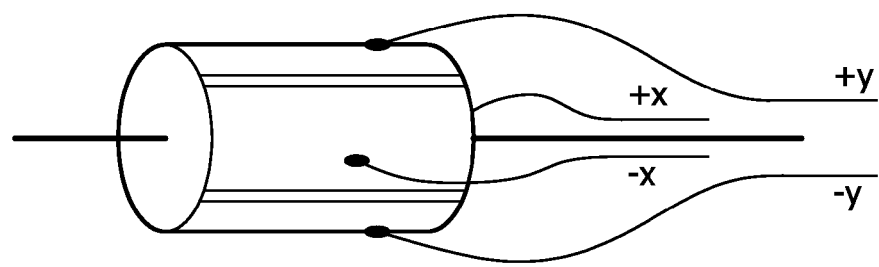
FIG. 9 shows an example of a resonant scanning pattern of a piezo drive fiber (prior art)
Figure 9B:
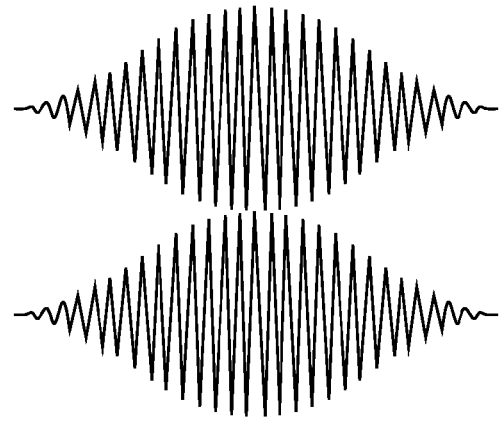
Figure 9C:
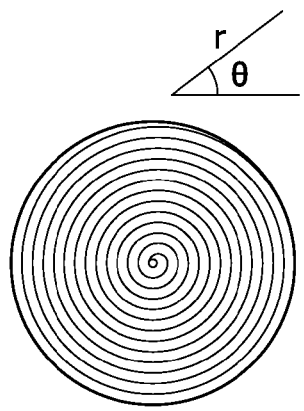

A fiber scanning system with coils and a magnet attached to the fiber is disclosed in FIG. 9 of U.S. Pat. No. 7,123,790. This system operates in a resonance mode, as the other prior art systems. The fiber scanning system according to the present embodiment has a number of features distinguishing it from that prior art system. These features include:

The orientation of the coils in the present system is 90 degrees rotated with respect to the prior art system.

The size of the magnet in the present system is increased with respect to the prior art system and now substantially overlaps the coils.

The coils in the present system are made shorter than the coils in the prior art system.

These features may all be applied simultaneously in order to arrive at the preferred system with its immanent advantages. These advantages include:
operable in a resonant and in a non-resonant mode, i.e. position the fiber at arbitrary positions in the working area,
relatively large working area for moving the fiber,
well-defined position of the fiber tip.

Furthermore, it is to be noted that it is common practice for creating a force between an electric coil and a magnet to use an orientation of the coil with respect to the magnet as is described in U.S. Pat. No. 7,123,790. Well-known applications like dynamos and motors all use such an orientation between coil and magnet.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A fiber scanning system comprising:
   housing (102) with a bottom and a wall,
   fiber (13), inside the housing (102), comprising a fixed part and a free end, the fixed part being attached to the bottom of the housing, the fiber (13) extending parallel to the wall of the housing (102),
   at least one electrical coil (12), attached to the wall at a position in between the fixed part and the free end of the fiber (13), a winding of the electrical coil (12) being in a plane parallel to the fiber (13), and
   magnet (11), attached to the fiber (13) at a position just before or after the electrical coil (12), a width of the magnet (11) being such that the magnet (11) extends over the electrical coil (12).

2. A fiber scanning system as claimed in claim 1, wherein the position of the magnet (11) is such that an air gap (16) between the electrical coil (12) and the magnet (11) is larger than 5 micrometer.

3. A fiber scanning system as claimed in claim 1, wherein the width of the magnet (11) is such that the magnet (11) extends over the electrical coil (12) for more than 10% of the coil length.

4. A fiber scanning system as claimed in claim 1, further comprising at least a second magnet (41, 51) attached to the fiber (13).

5. A fiber scanning system as claimed in claim 1, further comprising at least a second electrical coil (52).

6. A fiber scanning system as claimed in claim 1, wherein the magnet (11) is disk shaped.

7. A fiber scanning system as claimed in claim 1, wherein a distance between the fixed part of the fiber (13) and the magnet (11) is adjustable.

8. A fiber scanning system as claimed in claim 1, wherein a distance between the magnet (11) and the free end of the fiber (13) is adjustable.

9. A fiber scanning system according to claim 1, wherein the fiber (13) is a light guiding fiber.

10. A fiber scanning system according to claim 1, wherein the magnet (11) is a permanent magnet.

11. A medical device comprising:
    a fiber scanning system according to claim 1, further comprising
    a light source for sending light through the fiber (13) of the fiber scanning system,
    a light detector coupled to the fiber (13) for detecting reflected light,
    processing means coupled to the light detector for processing a signal from the light detector, and
    output means coupled to the processing means for providing the processed signal to a user.

12. A fiber scanning system according to claim 1, wherein the system is operable for scanning in a resonant mode.

13. A fiber scanning system according to claim 1, wherein the system is operable for scanning in a non resonant mode.

* * * * *